(12) United States Patent
Kataoka

(10) Patent No.: US 8,211,899 B2
(45) Date of Patent: Jul. 3, 2012

(54) ARTIFICIAL NUCLEIC ACID BASES AND THEIR USE IN BASE PAIRING NATURAL NUCLEIC ACID BASES

(75) Inventor: Masanori Kataoka, Okazaki (JP)

(73) Assignee: Inter-University Research Institute Corporation National Institute of Natural Sciences, Tokyo (JP)

( * ) Notice: Subject to any disclaimer, the term of this patent is extended or adjusted under 35 U.S.C. 154(b) by 559 days.

(21) Appl. No.: 12/064,858

(22) PCT Filed: Jul. 27, 2006

(86) PCT No.: PCT/JP2006/314834
§ 371 (c)(1),
(2), (4) Date: Oct. 22, 2009

(87) PCT Pub. No.: WO2007/026485
PCT Pub. Date: Mar. 8, 2007

(65) Prior Publication Data
US 2010/0036108 A1    Feb. 11, 2010

(30) Foreign Application Priority Data
Aug. 30, 2005 (JP) .................. 2005-248585

(51) Int. Cl.
  *A01N 43/90* (2006.01)
  *A61K 31/519* (2006.01)
  *C07D 487/00* (2006.01)
(52) U.S. Cl. .................. 514/262.1; 544/256
(58) Field of Classification Search .......... None
See application file for complete search history.

(56) References Cited

U.S. PATENT DOCUMENTS

| 2003/0152925 A1 | 8/2003 | Chun |
| 2003/0175749 A1 | 9/2003 | Chun |
| 2004/0171820 A1 | 9/2004 | Seela |
| 2005/0164184 A1 | 7/2005 | Chun |
| 2007/0148683 A1 | 6/2007 | Chun |

FOREIGN PATENT DOCUMENTS

| JP | 2003-528883 A | 9/2003 |
| JP | 2005-511096 | 4/2005 |
| WO | WO01/72762 | 10/2001 |
| WO | 03/050305 A | 2/2003 |
| WO | WO2007/026485 | 3/2007 |

OTHER PUBLICATIONS

Dorwald F. A. Side Reactions in Organic Synthesis, 2005, Wiley: VCH, Weinheim p. IX of Preface.*
Niess, et. al., Journal of Heterocyclic Chemistry (1970), 7(1), 243-4.*
http://www.sigmaaldrich.com/catalog/ProductDetail.do?lang=en&N4=346799|ALDRICH&N5=SEARCH_CONCAT_PNO|BRAND_KEY&F=SPEC, last accessed on Dec. 20, 2011.*
He, J., and Seela, F., "Base Pairing of 8-Aza-7-deazapurine-2,6-diamine Linked via the N(8)-Position to the DNA Backbone: Universal Base-Pairing Properties and Formation of Highly Stable Duplexes when Alternating with dT," Helvetica Chimica Acta. vol. 85, No. 5 pp. 1340-1354 (2002).
International Preliminary Report on Patentability (Chapter I of the Patent Cooperation Treaty) corresponding to International Patent Application No. PCT/JP2006/314834 dated Mar. 4, 2008.
International Search Report corresponding to International Patent Application No. PCT/JP2006/314834 dated Oct. 17, 2006.
Loakes et al., "Synthesis and Some Biochemical Properties of a Novel 5,6,7,8-Tetrahydropyrimido[4,5-c]pyridazine Nuceloside," Helvetica Chimica Acta. vol. 86, No. 4 pp. 1193-1204 (2003).
Ohtsuka et al., "An Alternative Approach to Deoxynucleotides as Hybridization Probes by Insertion of Deoxyinosine at Ambiguous Codon Positions," The Journal of Biological Chemistry. vol. 260, No. 5 pp. 2605-2608 (1985).

* cited by examiner

*Primary Examiner* — Jeffrey Murray
(74) *Attorney, Agent, or Firm* — Jenkins, Wilson, Taylor & Hunt, P.A.

(57) ABSTRACT

The present invention provides artificial universal base capable of base pairing nonspecifically with any of four kinds of natural nucleic acid bases (A, T, G, and C) without the function to specifically recognize pairing natural nucleic acid bases for base pair formation.
Universal base capable of base paring nonspecifically with four kinds of natural nucleic acid bases, wherein the universal base has a structure represented by the following chemical formula:

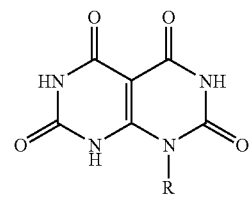

wherein R represents a monovalent group other than a hydrogen atom.

6 Claims, 2 Drawing Sheets

ARTIFICIAL NUCLEIC ACID BASES AND THEIR USE IN BASE PAIRING NATURAL NUCLEIC ACID BASES

FIELD OF THE INVENTION

This invention relates to a new type of universal base capable of forming a nonspecific base pair with four kinds of natural nucleic acid bases.

PRIOR ART

Many attempts to prepare a universal base, i.e. an artificial nucleic acid base capable of forming nonspecific pseudo base pairs with natural nucleic acid bases, have been made. However, conventional universal bases belong to a kind of intercalator and are incapable of forming pseudo base pairs with natural nucleic acid bases. On the other hand, although inosine-based derivatives have been known as universal bases capable of forming pseudo base pairs (References 1, 2 etc.), it is known recently that the derivatives form base pairs by acting like only guanine (Reference 3).

In the present invention, pyrimido [4,5-d]pyrimidine-2,4,5,7-tetraone and its derivatives, which the present inventors used as bases of the universal base, has been considered incapable of forming pseudo base pairs with natural nucleic acid bases (Reference 4).

Reference 1: Japanese Patent Application Disclosure No. 2005-511096 (WO2003/050305)
Reference 2: Japanese Patent Application Disclosure No. 2003-528883 (WO01/072762)
Reference 3: Ohtsuka, E. et al., J. Biol. Chem., 260, 2605-2608 (1985)
Reference 4: Niess, R., Robins, R. K. J., Heterocyclic. Chem., 7, 243-244 (1979).

Problems to be Solved by the Invention

It is an object of the present invention to provide an artificial nucleic acid base, which is capable of forming a nonspecific base pair with four kinds of natural nucleic acid bases (A, T, C and G) but has no function of forming a specific base pair with any of them.

Means to Solve the Problems

The present inventors focused on pyrimido [4,5-d]pyrimidine-2,4,5,7-tetraone represented by the following structure:

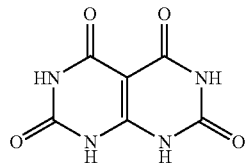

The solubility of an unsubstituted form of pyrimido [4,5-d]pyrimidine -2,4,5,7-tetraone in water and organic solvents is extremely low. Since base pairing with natural nucleic acid bases is usually performed in solution, low solubility of the compound deprives the compound of the function of base pairing, which is an object of the present invention. Consequently, introduction of alkyl group and the like except hydrogen atom at the position 1 of the compound by the present inventors led to increased solubility in water and organic solvents. Actually, it was confirmed that the solubility increased to the extent that the concentration was enough for base pairing with natural nucleic acid bases. Furthermore, test of base pairing with 4 kinds of natural nucleic acid bases confirmed nonspecific base pairing of the compound with any of four kinds of natural nucleic acid bases and resulted in accomplishment of the present invention.

Namely, the present invention is a universal base capable of base pairing nonspecifically with four kinds of natural nucleic acid bases, wherein the universal base has a structure represented by the following chemical formula:

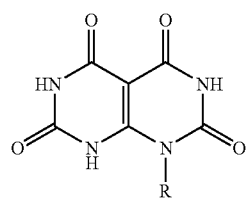

wherein R represents a group with mono valence, except hydrogen atom.

Furthermore, the present invention is a method for making base pairing, comprising mixing a solution containing natural nucleic acid bases or oligonucleotides comprising natural nucleic acid bases with the above universal base.

Advantages of the Invention

The universal base of the present invention is a novel compound with completely different structure from the compounds conventionally referred to as universal bases. The universal base forms pseudo base pair by changing the structure responding to the paring bases.

DETAILED DESCRIPTION OF THE INVENTION

Figure 1:
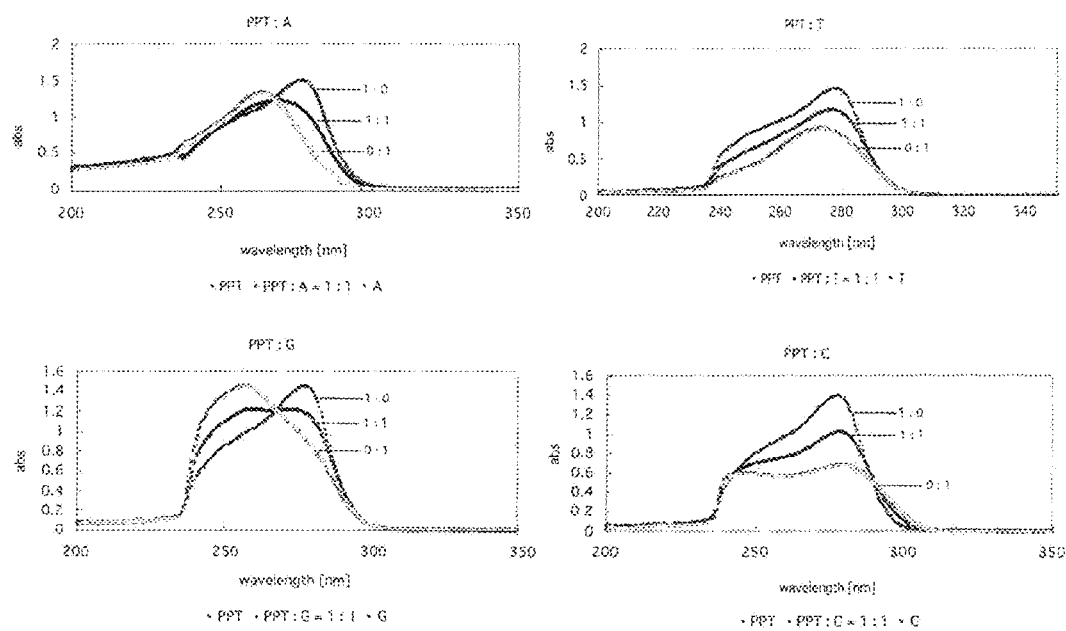
FIG. 1 shows the absorbance change of the mixture between the universal base (PPT) of the present invention and four kinds of natural nucleic acid bases.

The structure of universal base of the present invention is represented by pyrimido[4,5-d]pyrimidine-2,4,5,7-tetraone with a substituent group at nitrogen atom of position 1 as in chemical formulae 1:

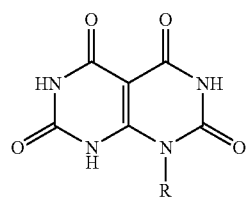

R is any group with mono valence except hydrogen atom. Preferably, the compound has enough solubility in the solution containing natural nucleic acid bases or oligonucleotides comprising natural nucleic acid bases to form a base pair with the solutes, and therefore has no obstacle to form a base pair.

To meet these requirements, R may be selected from the group comprising hydrocarbons containing hetero atoms (i.e. S, O, N and the like), such as alkyl, alkenyl, alkynyl, aryl or heterocyclic group; protein or peptide fragment; natural nucleic acid or other artificial nucleic acid; synthetic polymer such as styrene beads; and the like. Furthermore, the above groups may be labeled with various reactive groups or chromophores.

Moreover, R may be preferably a natural or artificial oligonucleotide chain in the case of cloning of sequence-unidentified gene or unidentified gene in PCR analysis; detection of single nucleotide polymorphism in human genome; suppression of expression of unidentified gene by anti-gene method. Alternatively, R may be preferably a water soluble functional group, such as alkyl group containing hydroxyl, thiol, carboxyl, amide or amidine in the case of highly selective extraction or removal of nucleic acid component. Furthermore, R may be preferably a lipid soluble functional group, such as alkyl containing alkyl with equal to or more than five carbon atoms, siloxy, ester or aryl in the case of highly selective extraction or removal of nucleotide component.

The universal base of the present invention can be convertible to both purine and pyrimidine types via rotation depending on the bonding. More specifically, as shown in the following structures, the universal base of the present invention is in amide type configuration in case of base pairing with an amidine type base such as adenine (A) or cytosine (C), and in amidine type configuration in case of base pairing with an amide type base, such as guanine (G) or thymine (T). Therefore, the universal base can form base pairing with all kinds of natural nucleic acid bases, as shown below:

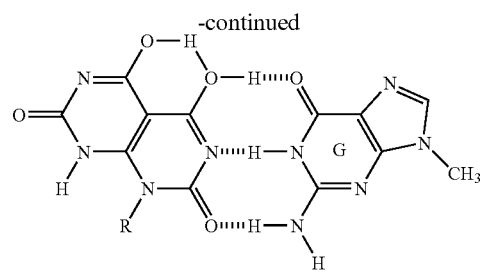

The solvent, which is used for base paring between the universal base of the present invention and natural nucleic acid bases, is preferably aprotic organic solvent generally. The solvent may be buffer solution when considering the solubility of DNA and the application in vivo; water or alcohol for synthesis or utilization of oligonucleotide; or DMSO or DMF contemplating for adsorption of nucleosides. The concentration of universal base and natural nucleic acid bases is generally about 1 mM for base pairing.

The following examples illustrate the present invention, but are not intended to limit the scope of the present invention.

EXAMPLES 1

Pyrimido [4,5-d]pyrimidine-2,4,5,7-tetraone derivatives (hereinafter referred to as "PPT") with the following structure was synthesized (R is —CH$_2$CH$_2$OTBDPS):

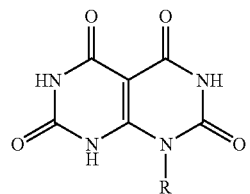

The reaction scheme is as follows:

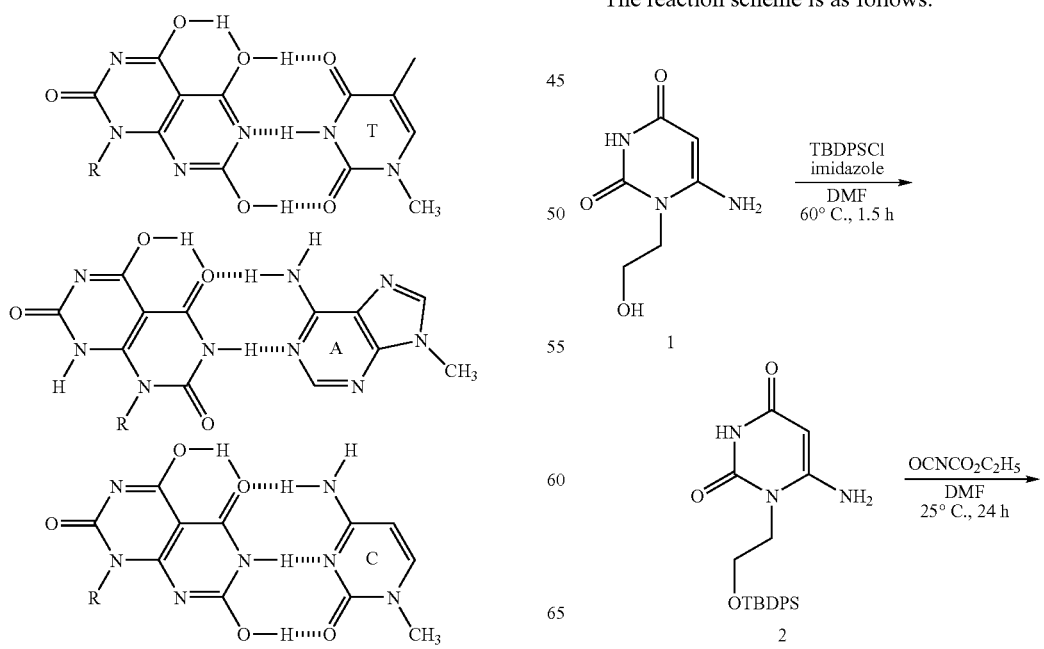

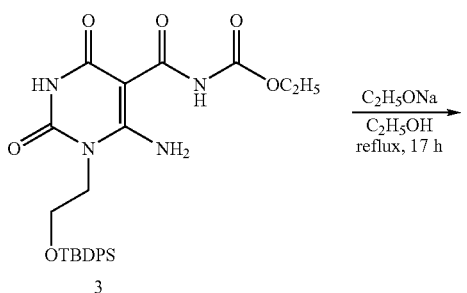

3

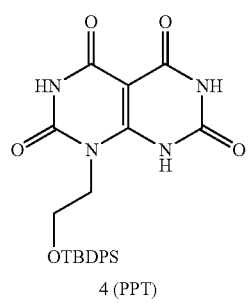

4 (PPT)

Synthesis of 1-hydroxy-ethyl-6-aminouracil (Compound 1)

Metal sodium (2.8 g, 120 mmol) was added carefully in 90 mL of ethanol anhydride in a 200 mL mad apple-type flask with a stirrer coated with fluoropolymer in ice bath with constant stirring and was completely dissolved. Then, 6.3 g (60 mmol) of hydroxyethylurea and 6.4 mL (60 mmol) of ethylcyanoacetate were added and refluxed for seven hr. The obtained solution was filtrated, washed with ethanol, solubilized in water, neutralized with 1.0 M diluted hydrochloric acid, filtrated and provided white pellets, which were recrystallized in water and gave compound 1 as a white crystal (6.1 g, 35.6 mmol, yield: 59.4%); $^1$H NMR (DMSO-d6, 400 MHz): δ 3.54 (t, 2H, NCH$_2$CH$_2$, 9.6 Hz), 3.83 (t, 2H, CH$_2$OH, 9.6 Hz), 4.57 (br, 1H, CHCNH$_2$), 5.09 (br, 1H, OH), 6.61 (br, 2H, NH$_2$), 10.32 (br, 1H, NH); $^{13}$C NMR (DMSO-d6, 100 MHz): δ 44.13 (NaC$_2$CH$_2$), 59.28 (CH$_2$OH), 76.52 (CHCNH$_2$), 151.87, 157.04, 162.89.

Synthesis of 1-(2-t-butyldiphenylsilaniloxy) ethyl-6-aminouracil (Compound 2)

The compound 1 obtained above (1.0 g, 5.8 mmol), t-butyl-diphenyl-chlorosilane (Tokyo Chemical Industry Co., Ltd., 1.7 mL, 6.4 mmol), imidazole (Nacalai Tesque Ltd., 875 mg, 12.8 mmol), 6 mL of dimethyl formamide (Kishida Chemical Co., Ltd.,) were added to 50 ml mad apple-type flask with a stirrer coated with fluoropolymer, were subjected to reaction at 60° C. for 1.5 hr., and then were dropped slowly to 1 L of water by the use of Pasteur pipette with constant stirring for a while, filtrated, dried, and gave compound 2 as white solid (2.2 g, 5.4 mmol, yield: 92.0%).

$^1$H NMR (DMSO-d6, 400 MHz): δ 0.96 (s, 9H, C(CH$_3$)$_3$), 3.76 (br, 2H, NCH$_2$), 4.04 (br, 2H, CH$_2$OH), 4.60 (br, 1H, CHCNH$_2$), 6.70 (br, 2H, NH$_2$), 7.41 (m, 6H), 7.58 (m, 4H), 10.32 (br, 1H, NH); $^{13}$C NMR (DMSO-d6, 100 MHz): δ 19.11 (SiC(CH$_3$)$_3$), 26.92 (SiC(C(CH$_3$)$_3$), 42.06 (NCH$_2$CH$_2$), 61.55 (NCH$_2$CH$_2$), 76.15 (CHCNH$_2$), 127.96, 128.33, 130.33, 130.08, 134.94, 135.48, 151.85, 158.75, 162.94.

Synthesis of (6-amino-1-[2-(t-butyldiphenylsilyloxy)-ethyl]-2,4-dioxo-1,2,3,4-tetrahydropyrimidine-5-carbonyl) ethyl-carbamate (Compound 3)

The above obtained compound 2 (13.7 g, 33.3 mmol) and dimethylformamide (40 mL) were added to 100 mL mad apple-type flask with a stirrer coated with fluoropolymer. Isocyanato ethyl formate (3.9 g, Tokyo Chemical Industry Co., Ltd., 33.9 mmol) was added to the mixture dropping through a dropping funnel for 30 min with constant stirring at room temperature. Then, the mixture was left stirring for 24 hr. at room temperature, concentrated under reduced pressure, dried under reduced pressure, washed with ethyl acetate and gave compound 3 as white solid (7.0 g, 13.3 mmol, yield: 40.1%).

$^1$H NMR (DMSO-d6, 400 MHz); δ 0.94 (s, 9H, Si(CH$_3$)$_3$), 1.22 (t, 3H, OCH$_2$CH$_3$, 7.2 Hz), 3.81 (br, 2H, NCH$_2$, 4.8 Hz), 4.12 (q, 2H, OCH$_2$CH$_3$, 4.8 Hz), 4.18 (t, 2H, NCH$_2$CH$_2$, 4.8 Hz), 7.42 (m, 6H), 7.53 (M, 4H), 8.36 (br, 1H), 10.85 (br, 1H), 11.35 (br, 1H), 12.39 (br, 1H); $^{13}$C NMR (DMSO-d6, 100 MHz): δ 14.68 (OCH$_2$CH$_3$), 19.05 (SiC(CH$_3$)$_3$), 26.89 (SiC(CH$_3$)$_3$), 43.12 (NCH$_2$), 60.61 (OCH$_2$CH$_3$), 61.12 (NCH$_2$CH$_2$), 81.06 (COCCO), 128.30, 130.39, 132.94, 135.42, 148.77, 150.77, 159.94, 164.45, 166.23.

Synthesis of 1-[2-(t-butyl-diphenyl-silyloxy)-ethyl]-1H,8H-pyrimido [4,5-d]pyrimidine-2,4,5,7-tetraone (Compound 4)

Metal sodium (Nacalai Tesque Ltd., 60 mg, 2.6 mmol) was added carefully in 20 mL of ethanol anhydride (Nacalai Tesque Ltd.) in a 50 mL mad apple-type flask with a stirrer coated with fluoropolymer in ice bath with constant stirring and was completely dissolved. Then, 600 mg (1.1 mmol) of the compound 3 obtained above was added to the above solution, refluxed for 17 hr. and provided reaction solution. The reaction solution was filtrated to provide solid precipitate, which was washed with 1.0 M diluted hydrochloric acid, dried under reduced pressure and gave compound 4 (PPT) as white solid (500 mg, 1.0 mmol, yield: 91.6%).

$^1$H NMR (DMSO-d6, 400 MHz): δ 0.94 (s, 9H, SiC(CH$_3$)$_3$), 3.83 (t, 2H, NCH$_2$CH$_2$), 4.23 (t, 2H, NCH$_2$CH$_2$), 7.38 (m, 6H), 7.57 (m, 4H), 9.79 (br, 1H), 10.53 (br, 1H); $^{13}$C NMR (DMSO-d6, 100 MHz): δ 19.16 (SiC(CH$_3$)$_3$), 27.03 (SiC(CH$_3$)$_3$), 42.27 (NCH$_2$), 61.12 (NCH$_2$CH$_2$), 86.04 (COCCO), 128.26, 130.14, 133.56, 135.43, 151.56, 157.86, 161.62, 162.60, 164.78, MS (ESI$^+$) 479.21 (M$^+$H$^+$ calcd 479.17)

EXAMPLE 2

The solubility of PPT obtained in Example 1 was examined. For comparison, the solubility of a PPT derivative, wherein R is H in chemical formula I (hereinafter, referred to as "PPT(H)"). For the solubility test, each solvent listed in Table I was used, and the concentration of solute was 1 to 100 mM. The solution with respective concentrations was warmed once to 50° C. and cooled to 27° C. The solution with residues was referred to as "insoluble", in the contrast the solution without residues was referred to as "soluble". The concentration of the buffer was 100 mM and the pH was 7.0. The results are shown in Table I.

TABLE I

| | | R | | | | | | | | |
|---|---|---|---|---|---|---|---|---|---|---|
| | | H | | CH2CH=CH2 | | CH2CH2OH | | CH2CH2OTBDPS | | CH2COOH |
| | | | | | | concentration | | | | |
| | | 1 mM | 100 mM | 1 mM | 100 mM | 1 mM | 100 mM | 1 mM | 100 mM | 1 mM | 100 mM |
| solvent | water | Ins | Ins | S | Ins | S | Ins | S | Ins | S | S |
| | phosphate buffer | Ins | Ins | S | Ins | S | Ins | S | Ins | S | S |
| | TBE buffer | Ins | Ins | S | Ins | S | Ins | S | Ins | S | S |
| | methanol | Ins | Ins | S | Ins | S | Ins | S | Ins | S | Ins |
| | DMSO | Ins | Ins | S | S | S | Ins | S | S | S | Ins |
| | DMF | Ins | Ins | S | S | S | Ins | S | S | S | Ins |

*Ins: insoluble. S: soluble

PPT (H) was insoluble in water and various organic solvents. However, 1-alkyl substituted PPT, wherein the alkyl group is simply methyl, ethyl or allyl, shows solubility with more than 100 μM. Solubility in aqueous solution is remarkably increased by introducing alkyl group with equal to or more than one carbon atom, which is functionalized with heterocyclic group, while solubility in organic solvent is remarkable increased by introducing alkyl group with equal to or more than three carbon atoms on nitrogen atom at position 1, or trialkyl siloxy group.

EXAMPLE 3

Pseudo base pairing between PPT and each of four kinds of natural nucleic acid bases was examined. The natural nucleic acid bases used were as follows:

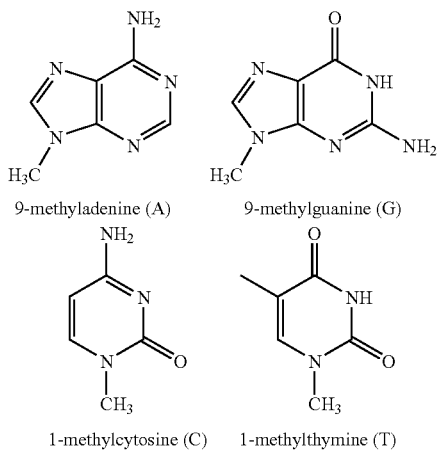

9-methyladenine (A)  9-methylguanine (G)
1-methylcytosine (C)  1-methylthymine (T)

The method of synthesis of the above bases are shown later in Synthetic Example 1. N-methylation was intended to interfere base pairing at position 1 and at position 9 for purines and pyrimidines, respectively.

The test of base pair formation was carried out in the following way. The concentration of the mixture of PPT and one of respective N-methylated natural nucleic acid bases (1-methylcytosine (herein after, referred to as "C"), 1-methylthymine (hereinafter, referred to as "T"). 9-methyladenine (hereinafter, referred to as "A"), and 9-methylguanine (hereinafter, referred to as "G")) was kept constant at 7.5 mmol/L and the ratio (mol ratio) of the mixture was varied from 0:10 to 10:0. The mixture was dissolved at 25° C. in anhydrous dimethyl sulfoxide (DMSO), which had been removed oxygen by freezing-degas method, dissolved argon gas, mixed with DMSO solution of substrates prepared before hand, and allowed to leave for overnight (12 hr.). Then, the change of absorbance in ultraviolet wavelength region was measured according to the following conditions:

(1) The measuring equipment, JASCO V-550 SERIAL NO. C02951260;
(2) The thermal controller, JASCO PSC-498T;
(3) The cell, GL Science Type: AB20-SQ-0.1 (Optical path is 0.1 mm);
(4) The cell adopter, CAS-10-1;
(5) The measured wavelength region, 200-350 nm.

The absorbance changes are shown in FIG. 1. The absorbance changed in accordance with the mixing ratios. Plot of the absorbance change versus to mixing ratios at a wavelength, where the absorbance change was observed, are shown in FIG. 2.

The absorbance of substrates is proportional to a mixing ratio of the substrates (Beer's law) in the case of no interaction between substrates. When the plots are deviated from the linear line determined by Beer's law, it suggests the presence of interactions between the two substrates.

Figure 2:
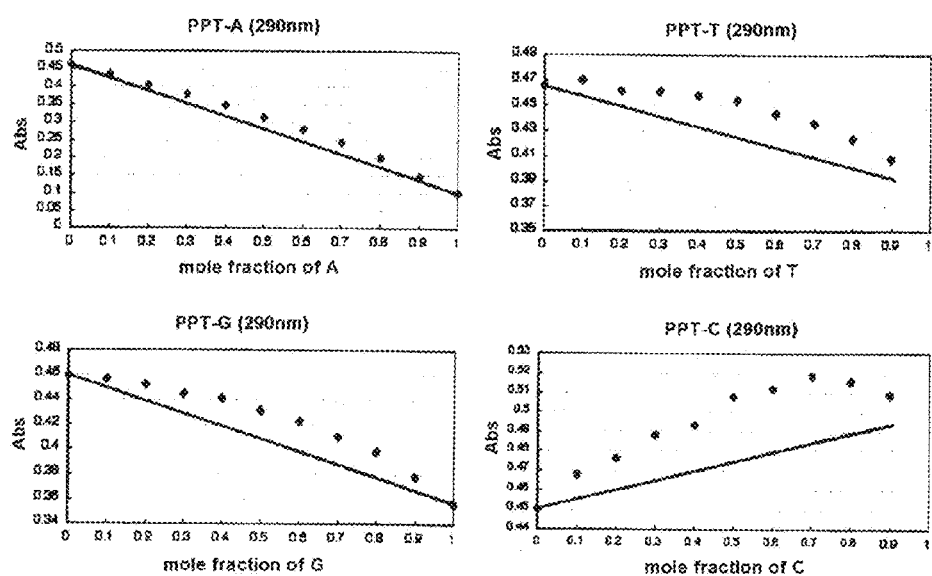
FIG. 2 shows a plot of the absorbance change of FIG. 1 versus mixing ratio.

As shown in FIG. 2, a large deviation from the linear line was observed for all mixture solution of the combination between PPT and any of the four kinds of natural nucleic acid bases. Therefore, it is conceivable that PPT and each natural nucleic acid base formed base pair and consequently the absorbance was deviated from the linear line by Beer's law.

COMPARATIVE EXAMPLE 1

Figure 3:
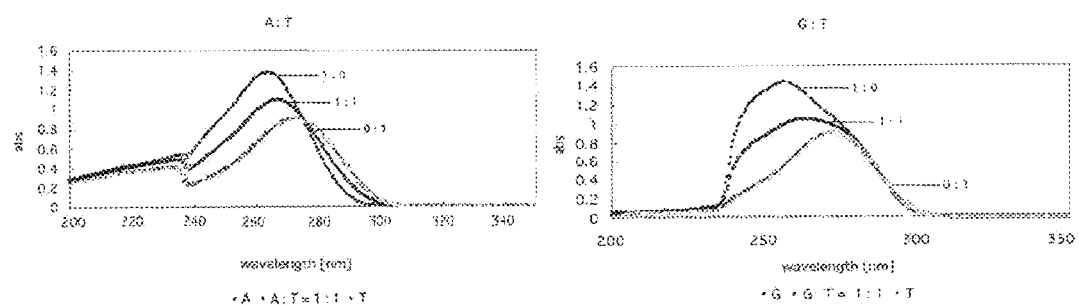
FIG. 3 shows the absorbance change of the mixture of A and T; and G and T.
Figure 4:
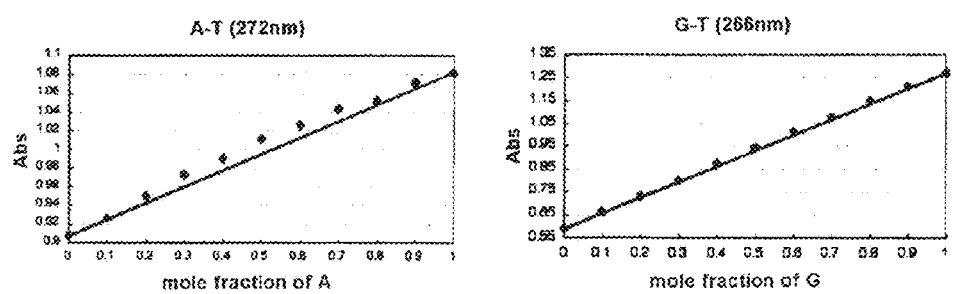
FIG. 4 shows a plot of the absorbance change of FIG. 3 versus mixing ratio.

For comparison, the base pair formation was examined for A and T, and G and T similarly to Example 3. The results are shown in FIGS. 3 and 4. While a deviation from the linear line by Beer's law ascribed to base pair formation was observed for A and T, no deviation from the linear line by Beer's law was observed for G and T, which indicates foming no base pair.

SYNTHETIC EXAMPLE 1

(1) Synthesis of 1-methylcytosine

Cytosine (3.0 g, 27 mmol) and dimethyl-formamide-dimethylacetal (40 mL) was added to 100 mL mad apple-type flask with a magnetic stirrer, heated at 120° C. with constant stirring. Then, trifluoroacetic acid (0.2 mL) was added and the mixture was allowed to stir for 18 hr. The reacting solution was cooled to room temperature, followed by cooling in ice bath. The white precipitation was filtrated, dissolved in dichloromethane and ethanol, and changed to powders by hexane. The solids were collected and dried under vacuum. Thus, 4-N—(N,N-dimethylaminomethylene)-1-methylcytosine was obtained as white solids (3.6 g, yield, 74%). ¹H-NMR (400 MHz, DMSO-d6)

4-N—(N,N-dimethyl-aminomethylene)-1-methylcytosine (1.0 g, 5.5 mmol) and ethanol solution (50 mL) containing 30% methylamine were added in 100 mL mad apple-type flask with a magnetic stirrer and the mixture was allowed to stir for 12 hr. The precipitated white solids were collected, and recrystallized in ethanol-water mixture. The object was obtained as white solids (0.61 g, yield, 88%). ¹H NMR (400 MHz, DMSO-d6):3.31 (s, 3H), 5.59 (d, 1H), 6.91 (br, 2H), 7.54 (d, 1H) ¹³C NMR (100 MHz, DMSO-d6):δ6.6, 92.9, 146.6, 156.3, 166.1; MS (ESI⁺) calcd for $C_5H_7N_3O+(M+H^+)$ 126.0662, found 126.0804.

(2) Synthesis of 1-methylthymine

Thymine (2.0 g, 16 mmol), hexamethyl-disilazane (32 mL) and trimethyl silylchloride (4.1 mL) were added in 100 mL mad apple-type flask with a magnetic stirrer and allowed to stir for 17 hr. at 140° C. until the reaction solution became transparent. After the reaction solution was cooled to 60° C., the solution was added with methyl-iodide (10 mL) and was allowed to stir for 29 hr. at 60° C. Then, the reaction solution was added with 6 N aqueous acetic acid solution (6 mL×10) and subjected to evaporation under reduced pressure. The residues were dissolved by the addition of 2-propanol and insolubles were filtered out. The filtrate was added with ethanol-water mixture. The object was recrystallized in ethanol-water mixture to give white solids (1.6 g, yield, 72%).

¹H NMR (400 MHz, DMSO-d6): δ 1.73 (d, 3H), 3.18 (d, 3H), 7.49 (t, 1H), 11.19 (br, 1H) ¹³C NMR (100 MHz, DMSO-d6): δ 11.9, 34.9, 108.1, 142.3, 151.2, 164.4; MS (ESI⁺) calcd for $C_6H_8N_2O_2+(M+H^+)$ 141.0608, found 141.0669.

(3) Synthesis of 9-methyladenine

Adenine (2.0 g, 14.8 mmol), tetrahydrofuran (100 mL) and tetrabutyl-ammonium-fluoride solution in 1.0 M tetrahydrofuran (37 mL, 37 mmol) were added in 300 mL mad apple-type flask with a magnetic stirrer. Methyl-iodide (2.72 mL) added drop wise to the solution in 10 minutes during stirring and allowed to stir for 2.5 hr. The reaction solution was evaporated under reduced pressure. The residues were dissolved in methanol and filtered. The filtrate was added ethanol-water mixture. The object was recrystallized in ethanol-water mixture to give white solids (1.0 g, yield, 45%). ¹H NMR (400 MHz, DMSO-d6): δ 3.70 (s, 3H), 7.15 (br, 2H), 8.07 (s, 1H), 8.13 (s, 1H), ¹³C NMR (100 MHz, DMSO-d6): δ 29.3, 118.6, 141.3, 149.8, 152.4, 155.9; MS (ESI⁺)calcd for $C_6H_7N_5^+(M^+H^+)$ 150.0774, found 150.0914.

(4) Synthesis of 9-methylguanine

A methyl group was introduced into 2-amino-6-chloro-9-methylpurine, a starting material, according to a reference. Purification using a column, which is described in the reference, was omitted and the procedure proceeded to the next step.

Benzyl alcohol (40 ml) and metal sodium (760 mg, 23.5 mmol) were added into 100 mL mad apple-type flask with a magnetic stirrer and were allowed to stir at room temperature for one hr. Then, 2-amino-6-chloro-9-methylpurine (1.98 g, 7.8 mmol) was added to the mixture and the mixture was allowed to stir at 70° C. for 48 hr. The reaction solution was separated by the addition of ethyl acetate—water and the aqueous phase was extracted two times by ethyl acetate. The fraction of ethyl acetate was mixed with the previous organic phase, and the mixture was washed with saturated solution of sodium chloride, dried with anhydrous sodium sulphate, and concentrated under reduced pressure. The residues were purified with silica gel column chromatography (hexane:ethyl acetate=1:1, ethyl acetate: methanol=9:1) to give white solid of 6-O-benzyl-9-methyl guanine (1.2 g, total yield: 26%). ¹H NMR (400 MHz, DMSO-d6): δ 3.58 (s, 3H), 5.48 (s, 2H), 6.44 (br, 2H), 7.33-7.49 (m, 5H), 7.81 (s, 1H).

6-O-benzyl-9-methylguanine (1.48 g), dichloromethane (20 mL) and trifluoroacetic acid (10 mL) were added to 100 mL mad apple type flask and left for constant stirring at room temperature for 12 hr. After the reaction, the solvent was removed on the rotary evaporator and the residues were boiled with methanol. After the residues were dissolved in ethanol, the solution was changed to powders by the addition of hexane. The solids were collected, recrystallized in ethanol-water mixture and gave the object as white solid (0.7 g, yield: 75%).

¹H NMR (400 MHz, DMSO-d6): δ 3.51 (s, 1H), 6.40 (br, 2H), 7.61 (s, 1H), 10.49 (br, 1H) ¹³C NMR (100 MHz, DMSO-d6): δ 29.2, 116.5, 138.0, 151.5, 153.5, 156.8; MS (ESI⁺) calcd for $C_6H_7N_5O+(M+H^+)$ 166.0723, found 166.0860.

Industrial Applicability of the Invention

The universal base of the present invention can be applied to cloning of a gene without determined sequence and an unspecified gene by PCR, detection of single nucleotide polymorphism in human genome, suppression of unspecified gene expression by anti-gene method, or highly selective extraction/removal of nucleic acid component. In these cases, the universal base may be introduced into other artificial nucleic acid or into other biological-mimetic material, or supported by polystyrene beads depending on the application. Moreover, the universal base element may be applied to selective removal or isolation of nucleotide components.

What is claimed is:

1. A compound having a structure represented by the following chemical formula:

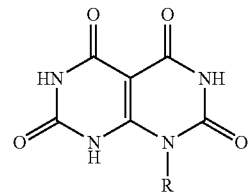

wherein R comprises (a) a natural or artificial oligonucleotide chain; (b) an alkyl group containing a hydroxyl, thiol, carboxyl, amide or amidine; (c) an alkyl group with three or more carbon atoms; (d) an alkyl group containing a siloxy, ester or aryl; or (e) alkenyl, alkynyl, aryl, heterocycle, or hydrocarbon containing a heteroatom.

2. The compound of claim 1, wherein R is a natural or artificial oligonucleotide chain.

3. The compound of claim 1, wherein R is an alkyl group containing a hydroxyl, thiol, carboxyl, amide, or amidine.

4. The compound of claim 1, wherein R is alkyl with three or more carbon atoms or alkyl containing siloxy, ester or aryl.

5. A compound having a structure represented by the following chemical formula:

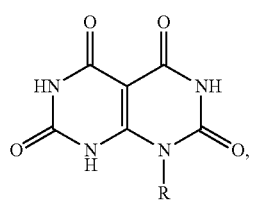
wherein R is alkenyl, alkylhydroxy, alkylcarboxy, or alkylsilylether.
6. A method for base pairing nucleic acid bases, comprising mixing a solution containing natural nucleic acid bases or oligonucleotides comprising natural nucleic acid bases with the compound of claim 1 or claim 5.
* * * * *